(12) United States Patent
Christiansen

(10) Patent No.: US 6,974,320 B2
(45) Date of Patent: *Dec. 13, 2005

(54) TOOLS AND METHODS FOR MEASURING TOOTH REDUCTION

(76) Inventor: Bart G. Christiansen, 38666 County Rd. 21, Elizabeth, CO (US) 80107

( * ) Notice: Subject to any disclaimer, the term of this patent is extended or adjusted under 35 U.S.C. 154(b) by 0 days.

This patent is subject to a terminal disclaimer.

(21) Appl. No.: 10/637,988

(22) Filed: Aug. 8, 2003

(65) Prior Publication Data
US 2004/0063061 A1 Apr. 1, 2004

Related U.S. Application Data

(63) Continuation-in-part of application No. 10/116,174, filed on Apr. 3, 2002, now Pat. No. 6,752,628.

(51) Int. Cl.⁷ ................................................ A61C 9/00
(52) U.S. Cl. ............................ 433/70; 433/218; 433/75
(58) Field of Search ........................... 433/70, 75, 218, 433/219, 72, 68; 33/513, 514, 514.4, 555.4, 602; 132/321

(56) References Cited

U.S. PATENT DOCUMENTS

| | | | | |
|---|---|---|---|---|
| 855,875 A | * | 6/1907 | Bode | 33/514 |
| 861,874 A | * | 7/1907 | Macy | 33/514 |
| 955,320 A | * | 4/1910 | Cloud | 33/514 |
| 1,482,530 A | * | 2/1924 | Richardson | 33/514 |
| 2,280,486 A | * | 4/1942 | Hendy | 30/116 |
| 2,327,548 A | * | 8/1943 | Pearlman | 433/219 |
| 3,889,382 A | * | 6/1975 | Husted et al. | 33/514 |
| 4,304,246 A | * | 12/1981 | Yafai | 132/323 |
| 4,440,184 A | * | 4/1984 | Smith | 132/323 |
| 4,836,226 A | * | 6/1989 | Wolak | 132/321 |
| 5,525,059 A | | 6/1996 | Lee | |
| 5,732,721 A | * | 3/1998 | Pelok | 132/321 |
| 6,039,054 A | * | 3/2000 | Park et al. | 132/321 |
| 6,183,256 B1 | | 2/2001 | Fisher et al. | |
| 6,186,789 B1 | | 2/2001 | Hugo et al. | |
| 6,240,808 B1 | * | 6/2001 | Gelbard | 81/3.09 |

\* cited by examiner

*Primary Examiner*—Todd E. Manahan
(74) *Attorney, Agent, or Firm*—Townsend and Townsend and Crew LLP

(57) ABSTRACT

A tooth reduction measuring system comprises a holding tool having a proximal end and a distal end. A flexible loop extends from the distal end and defines an opening. The loop has a thickness from the range about 1 mm to about 2 mm, and the opening a size large enough to be placed around a tooth. The loop is adapted to be positioned relative to a pair of opposing teeth, one of which has been reduced. In this way, the pair of opposing teeth are within the opening, and the loop may be pulled by the shaft into a gap between the opposing teeth to permit evaluation of the size of the gap based on the thickness of the loop.

20 Claims, 8 Drawing Sheets

TOOLS AND METHODS FOR MEASURING TOOTH REDUCTION

CROSS REFERENCE TO RELATED APPLICATIONS

This application is a continuation in part application and claims the benefit of U.S. application Ser. No. 10/116,174, filed Apr. 3, 2002, now U.S. Pat. No. 6,752,628 the complete disclosure of which is herein incorporated by reference.

BACKGROUND OF THE INVENTION

This invention relates generally to the field of dentistry, and in particular to the reduction of teeth to facilitate placement of a dental prosthetic device, such as a crown. Or specifically, the invention is related to a dental tool and methods for measuring the amount of tooth reduction.

Artificial dental crowns are used as a restoration for teeth, and are particularly useful when teeth have been broken, have been weakened by decay, or have one or more large fillings. Dental crowns are constructed to fit over the remaining portion of the tooth to make the tooth stronger and provide the tooth with the shape and contour of the natural tooth. As such, crowns are often referred to as caps.

Dental crowns are typically fabricated outside the patient's mouth and then installed in the mouth. The manner of installation may vary depending on the nature of the crown. For example, full crowns are employed to cover the entire surface of a tooth as well as the sides of the tooth. Partial crowns are inlays which cover the top surface and portions of the sides. Inlays are employed to cover central portions of the top surface and may also extend partially onto the sides. Finally, veneers are used to cover a side surface of a tooth. A detailed discussion of how such dental crowns may be placed onto a tooth is set forth in U.S. Pat. No. 5,525,059, the complete disclosure of which is herein incorporated by reference.

Dental crowns may be employed to treat a variety of conditions. For example, as previously mentioned, the tooth may have been previously weakened by decay or may have a very large filling. Another reason for using a crown is if the individual has discolored fillings and would like to improve the appearance of the tooth. As a further example, the patient may have had an endodontic treatment of the root requiring protection of the remaining tooth.

Dental crowns may be constructed of a variety of materials. For example, the crown may be constructed of a porcelain that is bonded to a precious metal. In such cases, the precious metal is used to form the base and the porcelain is applied in layers over the metal base. As another example, the crown may be constructed entirely of porcelain. Because these look very natural, they may often be used for the front teeth. Other examples include porcelain and composite resin materials, glass, and precious metals, such as gold, platinum and palladium. A further description of materials used for dental crowns and how they may be bonded to the underlying tooth is set forth in U.S. Pat. No. 6,183,256, the complete disclosure of which is herein incorporated by reference.

In order to receive a crown, the dentist must first alter the shape of the tooth to a size and shape most conducive for receiving a crown. To do so, the dentist will typically remove most of the outer surface of the tooth, leaving a strong inner core. Ideally, the amount of tooth removed will be about the same as the thickness of the crown to be fitted. After the tooth has been formed to the proper shape, an impression of the prepared tooth along with the opposing jaw is used to determine the manner in which the teeth are brought together when the patient bites down. The impressions are then used by a dental technician to fabricate the crown to the shape of the reduced tooth.

Determining the appropriate size and shape of the tooth to be fitted with a crown is a difficult process, especially when the tooth is near the back of the patient's mouth. In such cases, it is nearly impossible to determine the amount of tooth that has been removed. However, determination of the amount of reduction is critical in order to ensure that the crown will properly fit. For example, if the tooth is-reduced too much, the crown may not fit properly. On the other hand, if the occlusal surface is not sufficiently reduced, the crown will be too large and will interfere with the patient's bite.

In order to determine the amount of tooth reduction, some have proposed the use of a thin rubber strip upon which the patient is instructed to bite. If the dentist is unable to pull the rubber strip from the patient's mouth, the dentist assumes that the tooth has not been sufficiently reduced in size. However, for teeth near the back of the patient's mouth, it is nearly impossible to appropriately position such a rubber strip in the patient's mouth.

Hence, this invention relates to a tooth reduction measuring tool along with methods for its use to facilitate proper tooth reduction when preparing for a crown.

BRIEF SUMMARY OF THE INVENTION

In one embodiment, the invention provides a tooth reduction measuring system that comprises a holding tool having a proximal end and a distal end. A connector is provided at the distal end. The system also includes a flexible loop that may be coupled to the holding tool by-the connector. For example, the connector may comprise a grasping mechanism, such as a pair of jaws, that are used to grasp the connector. The loop may have a thickness in the range from about 1 mm to about 2 mm and have an opening that is sized large enough to be placed around a tooth. In use, the loop may be positioned relative to a pair of opposing teeth, one of which has been reduced, such that the pair of opposing teeth are within the opening. The loop may be pulled by the holding tool into a gap between the opposing teeth to permit evaluation of the size of the gap based on the thickness of the loop.

To operate the grasping mechanism, the tool may include a pair of handles. Examples of tools that may operate in this way include hemostats, clamps, forceps and the like.

In another embodiment, the invention provides a tooth reduction measuring tool that comprises a shaft having a proximal end and a distal end, with the proximal end defining a handle. A flexible loop extends from the distal end and has a thickness in the range from about 1 mm to about 2 mm. The loop defines an opening that is sufficiently large to be placed around a tooth. In this way, the loop may be positioned relative to a pair of opposing teeth, one of which has been reduced, such that the pair of opposing teeth are within the opening. After instructing the patient to bite down, the shaft may be pulled to move the loop into a gap between the opposing teeth to permit the dentist to evaluate the size of the gap based on the thickness of the loop. For example, if the dentist is unable to pull the loop through the gap, the dentist may determine that the tooth needs to be further reduced, at least on the back side of the tooth. Alternatively, the dentist may choose another measuring tool with a loop having a smaller thickness and repeat the process to determine approximately how much more of the tooth needs to be reduced.

Optionally, the loop may include a marking material that produces a mark when engaging the tooth. In this way, when the dentist pulls on the loop and it engages the tooth, a mark will be produced on a loop or the tooth. The dentist may then evaluate the position of the mark to determine the location where additional tooth reduction needs to occur.

In another aspect, the loop may be constructed of a polymer so that the tool may be constructed in a relatively inexpensive manner. Further, the shaft may also be constructed of a polymer and integrally formed with the loop. In this way, the measuring tool may be disposed of after use. Further, the measuring tool may be placed into a sterile package so that the measuring tool will remain sterile until use.

To place a crown on a tooth, an initial amount of tooth structure is removed from the target tooth. The amount of removed tooth structure is then measured by grasping the measuring tool and placing the loop around or adjacent to the target tooth. The patient is then instructed to bite down to move an opposing tooth into position generally adjacent to the target tooth. The tool may then been retracted to pull the loop into a gap between the target tooth and the opposing tooth. The size of the gap may then be evaluated based on the thickness of the tooth relative to the gap as previously described. If needed, additional tooth structure may be removed from the target tooth or the opposing tooth if the loop is unable to move through the gap. Once the target tooth is appropriately sized and shaped, an impression may be taken and a crown formed. Following fabrication of the crown, it may be bonded to the target tooth.

In some cases, the loop may extend from the shaft at an acute angle to facilitate manipulation of the loop when measuring the back teeth. Alternatively, the loop may extend axially from the handle.

In some cases, the loop may be sold as a package, with the loops being connected to a frame or other packaging material. In this way, a loop may be separated from the frame and coupled to the tool prior to use. Following use, the loop may be discarded and the tool may be sterilized. Another loop may then be used with the tool.

DETAILED DESCRIPTION OF THE INVENTION

Figure 1:
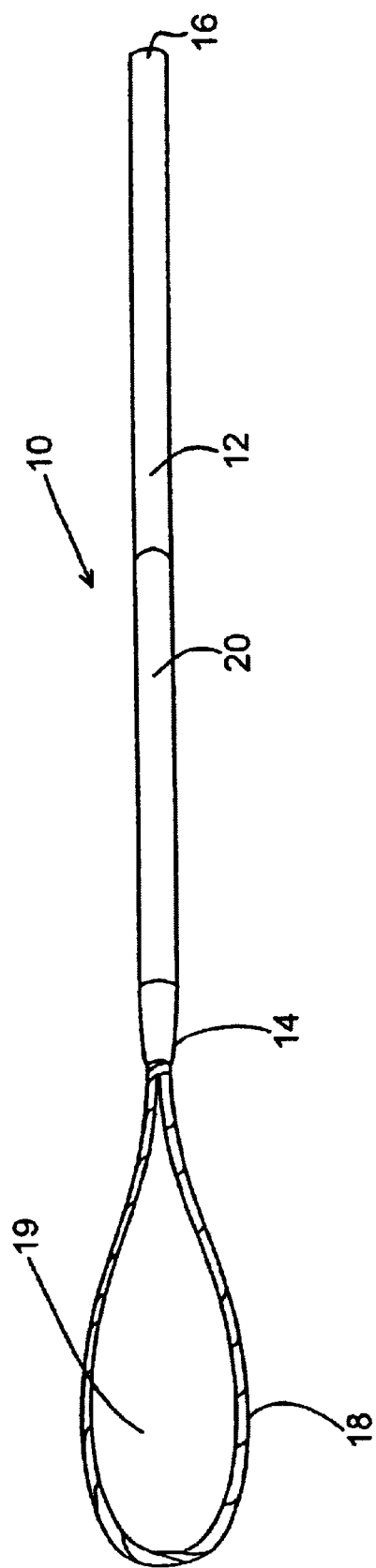
FIG. 1 is a top view of one embodiment of a tooth reduction measuring tool according to the invention.

The invention provides various tools and techniques for determining the amount of tooth reduction when preparing a tooth to receive an artificial dental crown. Once the tooth is appropriately prepared, the tooth may be fitted with a wide variety of dental crowns that are constructed of a wide variety of materials, such as those previously described in the background section of this application. Hence, the invention is not intended to be limited for use with only a specific type of dental crown. Further, the invention may also be used with a wide variety of techniques and tools that are employed to alter the shape of the tooth during preparation of the tooth. Hence, the invention is also not intended to be limited to a specific method for altering the shape and/or size of the tooth.

To measure the amount of tooth reduction, the invention utilizes a flexible loop that is positioned over the reduced tooth while the patient's mouth is open. The patient is then instructed to bite down and the loop is manipulated in an attempt to slide the loop between a gap defined by the reduced tooth and the opposing tooth. The thickness of the flexible loop may be selected such that if it cleanly passes through this gap, an appropriate amount of material has been removed. Conveniently, loops of different sizes may be used in an iterative process to prevent the over-reduction of a tooth. For example, a loop with a smaller thickness may initially be used. Once this cleanly passes through the gap, a loop with a larger thickness may be attempted to see if it will pass through the gap. The second loop may be of the desired thickness so that if the second loop fails to be pulled through the gap, the dentist may remove additional material until the second loop passes between the gap.

To help determine where additional material needs to be removed, the loop may include a marking material that produces a mark where it comes into contact with the tooth. Examples of marking materials include occlusal marking paper, such as that sold by G. E. Rudichhauser.

The loop may be held by essentially any type of tool or device that permits the loop to be inserted into the mouth and manipulated between the teeth. The loop may be integrally coupled to a tool or a handle or may be removably coupled to such a tool or device. This may be an off the shelf tool or one that is specifically manufactured for this application. For example, a tool such as a hemostat, pliers, clamps, forceps and the like may be used to grasp and hold the loop. Following use, the loop may be discarded and the tool reused. Loops may be sold separately or in packages so that following sterilization the tool may be reused with another loop.

Once the tooth has been appropriately prepared, the crown may be fabricated and coupled to the tooth using technique s known in the art. As such, the invention is not intended to be limited to a specific technique for forming and attaching a crown, but may use any of the techniques known to those skilled in the art.

Referring now to FIG. 1, one embodiment of a tooth reduction measuring tool 10 will be described. Measuring tool 10 comprises a shaft or handle 12 having a distal end 14 and a proximal end 16. Coupled to distal end 14 is a flexible loop 18. Loop 18 defines an opening 19 that is configured to be large enough to receive a patient's tooth. For instance, the cross sectional area of opening 19 may be in the range from about 25 mm² to about 175 mm², and more preferably from about 50 mm² to about 95 mm².

Shaft 12 is preferably rigid or semi-rigid to provide a convenient way to grasp measuring tool 10 and to manipulate loop 18 as described hereinafter. Conveniently, a roughened or serrated portion 20 may be provided on shaft 12 to facilitate grasping of shaft 12 when performing a procedure. A wide variety of materials may be used to construct shaft 12, such as stainless steel, plastics, composites, and the like. In some cases, it may be advantageous to construct shaft 12 of a polymer to reduce the overall cost of measuring tool 10 and to permit it to be disposed of after a single use. Shaft 12 may have a variety of external shapes, such as round, oval, triangular, and the like. Typically, the thickness of shaft 12 will be large enough to facilitate easy grasping while also being small enough to be easily manipulated within the patient's mouth. For example, for a circular shaft, the diameter may be in the range from about 2 mm to about 10 mm, and more preferably from about 3 mm to about 5 mm. Further, the length of shaft 12 is preferably long enough so that it can be used manipulate loop 18 to the reduced tooth without interfering with the dentist's movements. For instance, shaft 12 may have a length in the range from about 5 cm to about 15 cm.

Loop 18 is preferably constructed of a flexible material having a specified thickness. Examples of materials that may be used include polymers, flexible wires, braided materials, and the like. One advantage of constructing loop 18 and shaft 12 of the same material is that they may be integrally formed together during the manufacturing process. For example, if both are made of a polymer, a molding process may be used as known in the art to fabricate both shaft 12 and the loop 18. However, other techniques maybe used to couple loop 18 to shaft 12 as is known in the art.

Loop 18 may be provided with a variety of thicknesses to facilitate the measurement of a wide range of gaps between a patient's reduced tooth and the opposing tooth. For example, the flexible loop may have a thickness in the range from about 1 mm to about 2 mm. Further, measuring tool 10 may be fabricated in a variety of sizes, such as, for example, a measuring tool having a 1 mm loop, a measuring tool having a 1.5 mm loop, and a measuring tool having a 2 mm loop. In this way, the dentist may select the measuring tool with the appropriately sized flexible loop when measuring the size of the gap. Further, multiple measuring tools with different sized loops may be used in an iterative process when reducing the size and/or shape of the tooth as previously described.

In some embodiments, flexible loop 18 may also be provided with a marking material that produces a visible mark on loop 18 and the tooth when sufficient force is applied to loop 18. For example, if loop 18 is passed over a reduced tooth and shaft 12 is pulled, the locations where loop 18 contacts the reduced tooth and/or the opposing tooth is marked on loop 18. In this way, the dentist is provided with additional information about where additional tooth reduction is needed. An example of such a marking material is articulating paper.

Figure 2:
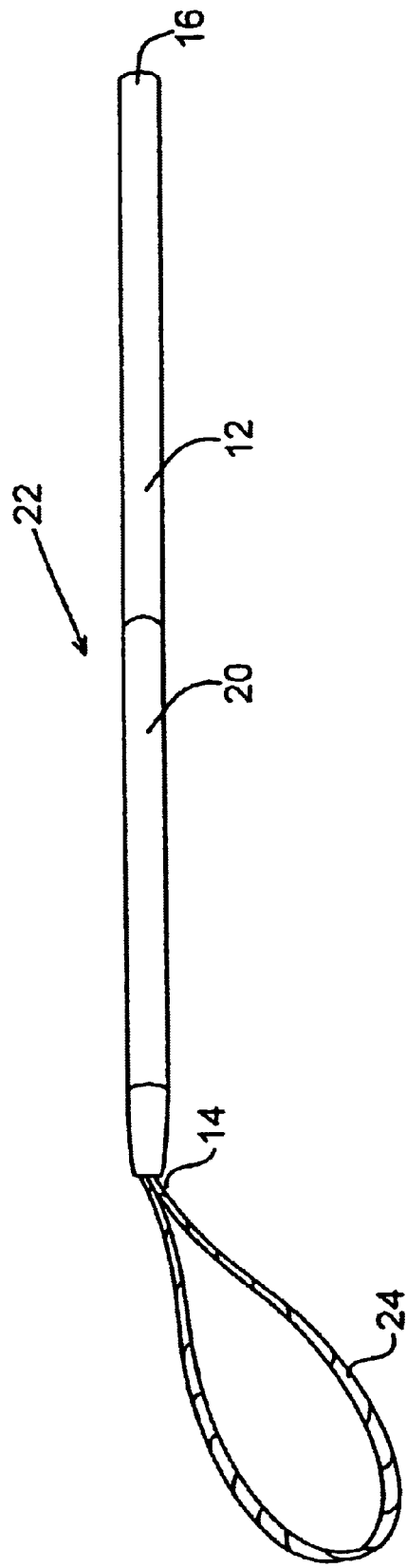
FIG. 2 illustrates another embodiment of a tooth reduction tool having an angled flexible loop according to the invention.

FIG. 2 illustrates an alternative embodiment of a tooth reduction measuring tool 22. Measuring tool 22 may employ the use of a shaft 12 that may be constructed in a manner similar to that previously described in connection with FIG. 1. Hence, the same reference numerals will be used to describe the same components of shaft 12. Extending from shaft 12 is a flexible loop 24 that may be constructed of the same types of materials used to construct loop 18 as previously described. In the embodiment of FIG. 2, loop 24 extends at an angle relative to the longitudinal axis extending through shaft 12. As shown, the angle between the axis and loop 24 is about 45 degrees. However, other angles may be used including angles from about 1 to about 90 degrees. Such an angling of loop 24 relative to shaft 12 may in certain circumstances permit easier introduction of loop 24 about a reduced tooth when performing a measurement.

Figure 3:
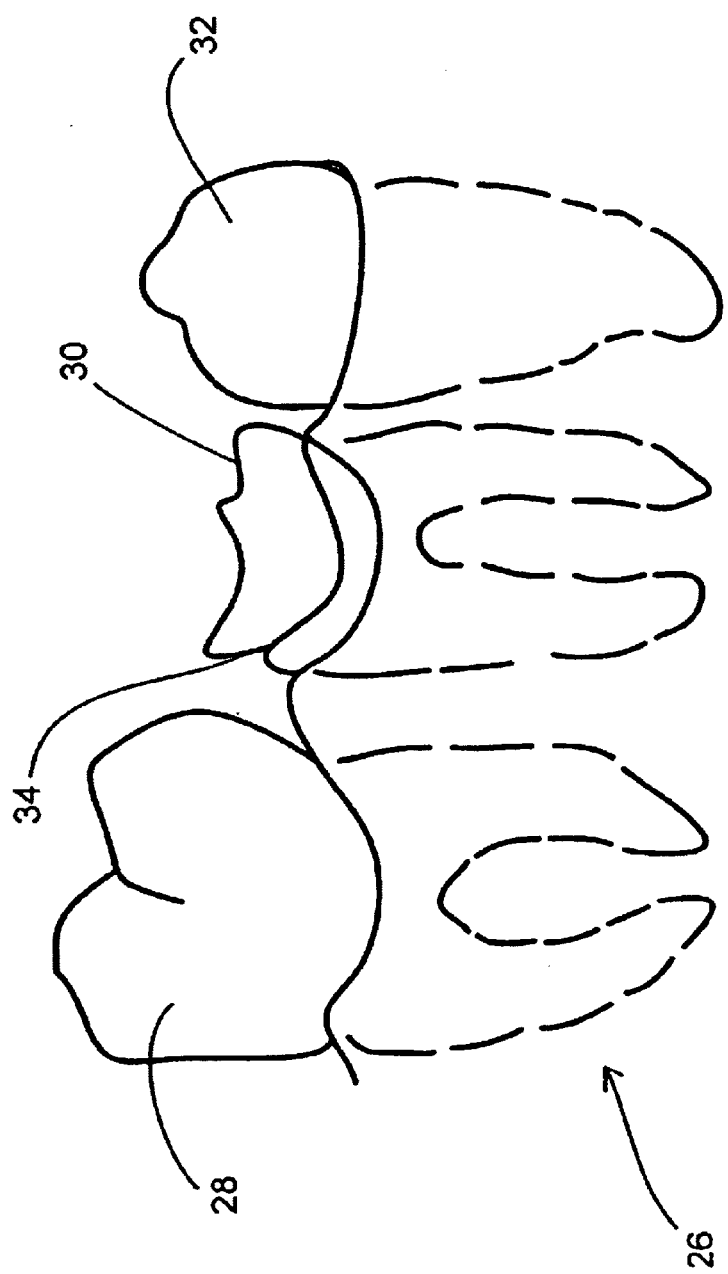
FIG. 3 is a side view of a portion of a patient's jaw showing a middle tooth that has been reduced in preparation for receiving a crown.
Figure 4:
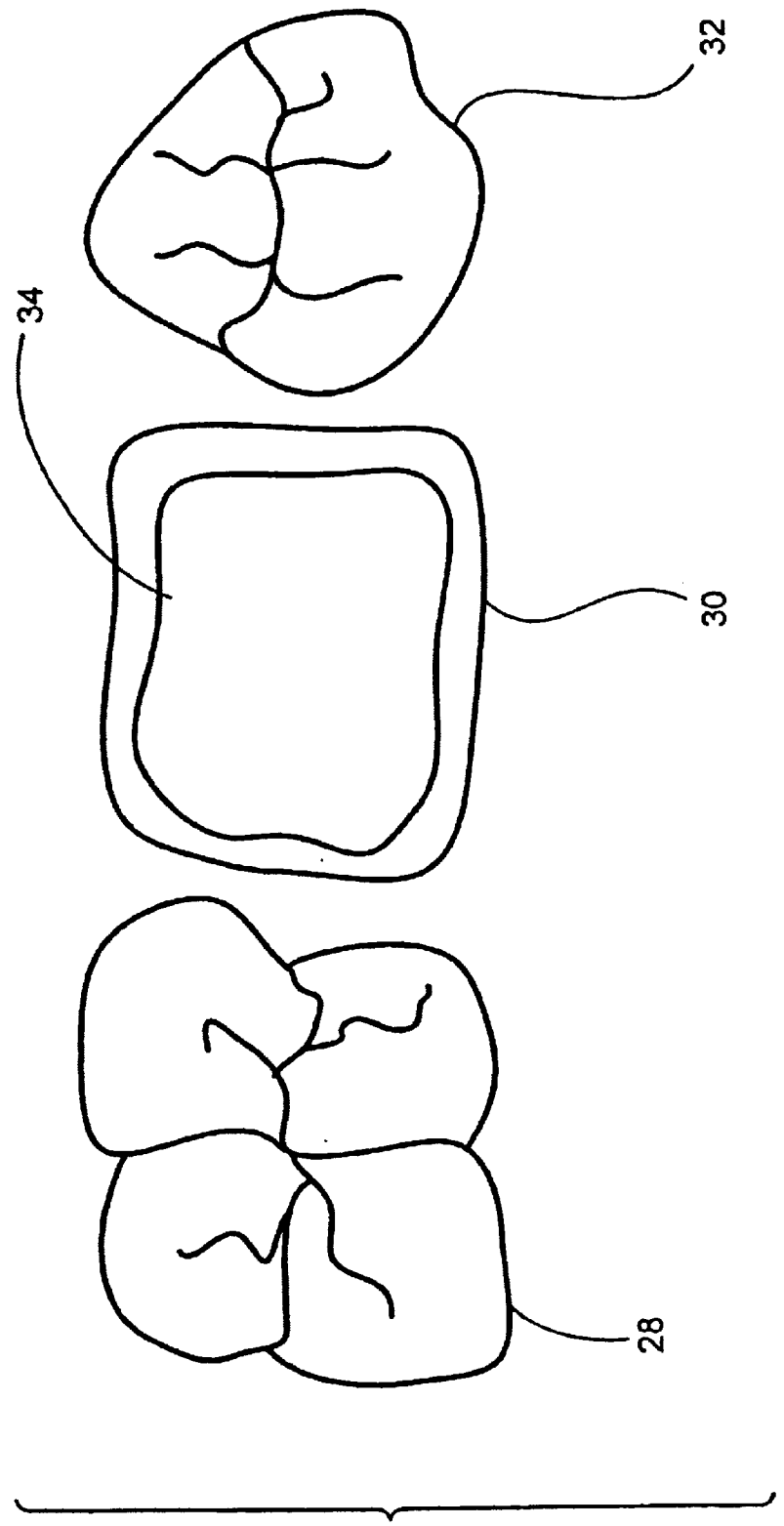
FIG. 4 is a top view of the teeth illustrated in FIG. 3.
Figure 5:
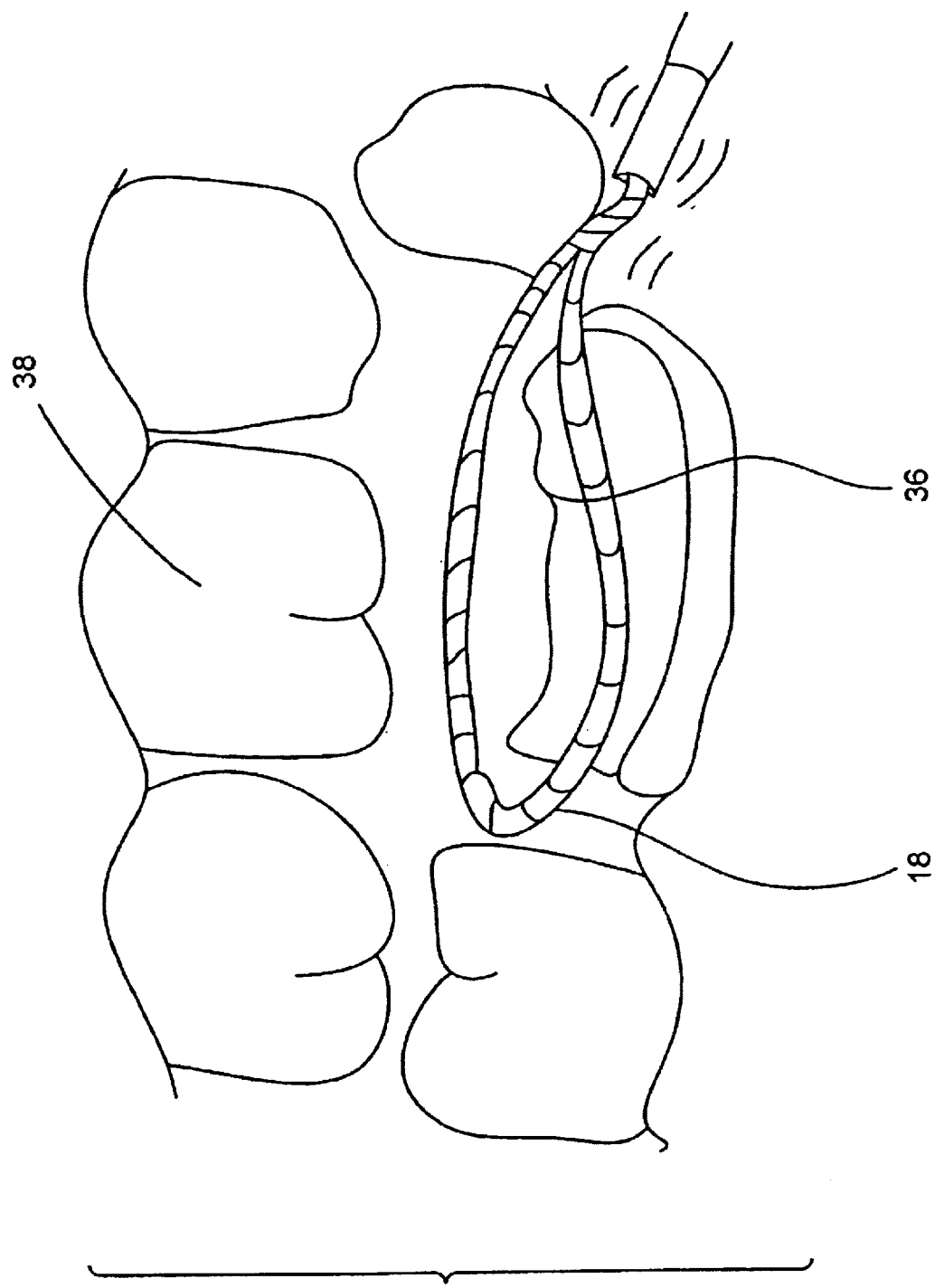
FIG. 5 illustrates a method for using the tooth reduction measuring tool of FIG. 1 to determine the amount of tooth reduction of the middle tooth of FIG. 3 according to the invention.
Figure 6:
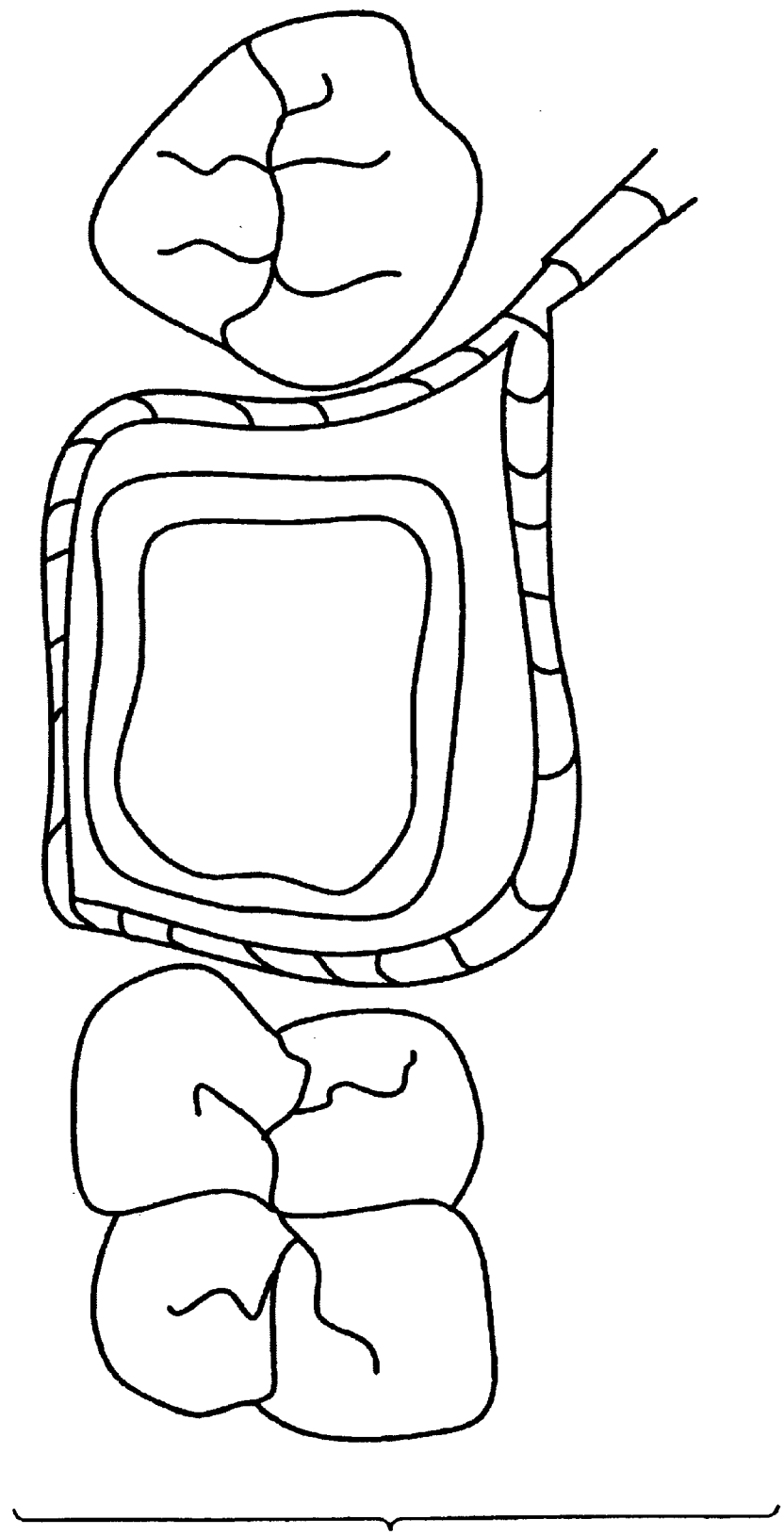
FIG. 6 is a top view of the middle tooth showing how the flexible loop of the tooth reduction measuring tool is positioned to measure the amount of reduction according to the invention.

Referring now to FIGS. 3–6, one method for measuring the amount of tooth reduction using measuring tool 10 will be described. Shown in FIG. 3 is a portion of a jaw 26 having teeth 28, 30 and 32. In describing the method, it will be appreciated that only a minimal number of teeth are shown to facilitate description of the inventive method. As such, it will be appreciated that the method may be employed with essentially any tooth in a patient's mouth that is being reduced. As best shown in FIGS. 3 and 4, tooth 30 has already experienced a procedure where a certain portion of the tooth has been reduced to form a reduced portion 34. Once reduced portion 34 is formed using any of the techniques known within the art, measuring tool 10 may be employed to measure the amount of reduction. This is accomplished by grasping shaft 12, typically between the thumb and first two fingers, and manipulating shaft 12 until loop 18 passes over tooth 30 as best shown in FIG. 5. Because of the spacing between teeth 28 and 30 and between teeth 30 and 32, as well as because of the amount of tooth reduction, loop 18 should fit around reduced portion 34 as best shown in FIG. 6. The patient is then instructed to bite down so that a gap 36 between tooth 30 and an opposing tooth 38 is formed. It is this gap that needs to be measured in order to properly fabricate the desired crown. While the patient remains biting, shaft 12 is manipulated in an attempt to pull loop 18 over tooth 30, with loop 18 passing through gap 36. If loop 18 is unable to pass through gap 36, the dentist may evaluate where loop 18 is engaging tooth 30 to determine where on tooth 30 additional material needs to be removed. To facilitate this evaluation, loop 18 may be provided with a marking material as previously described.

Figure 7:
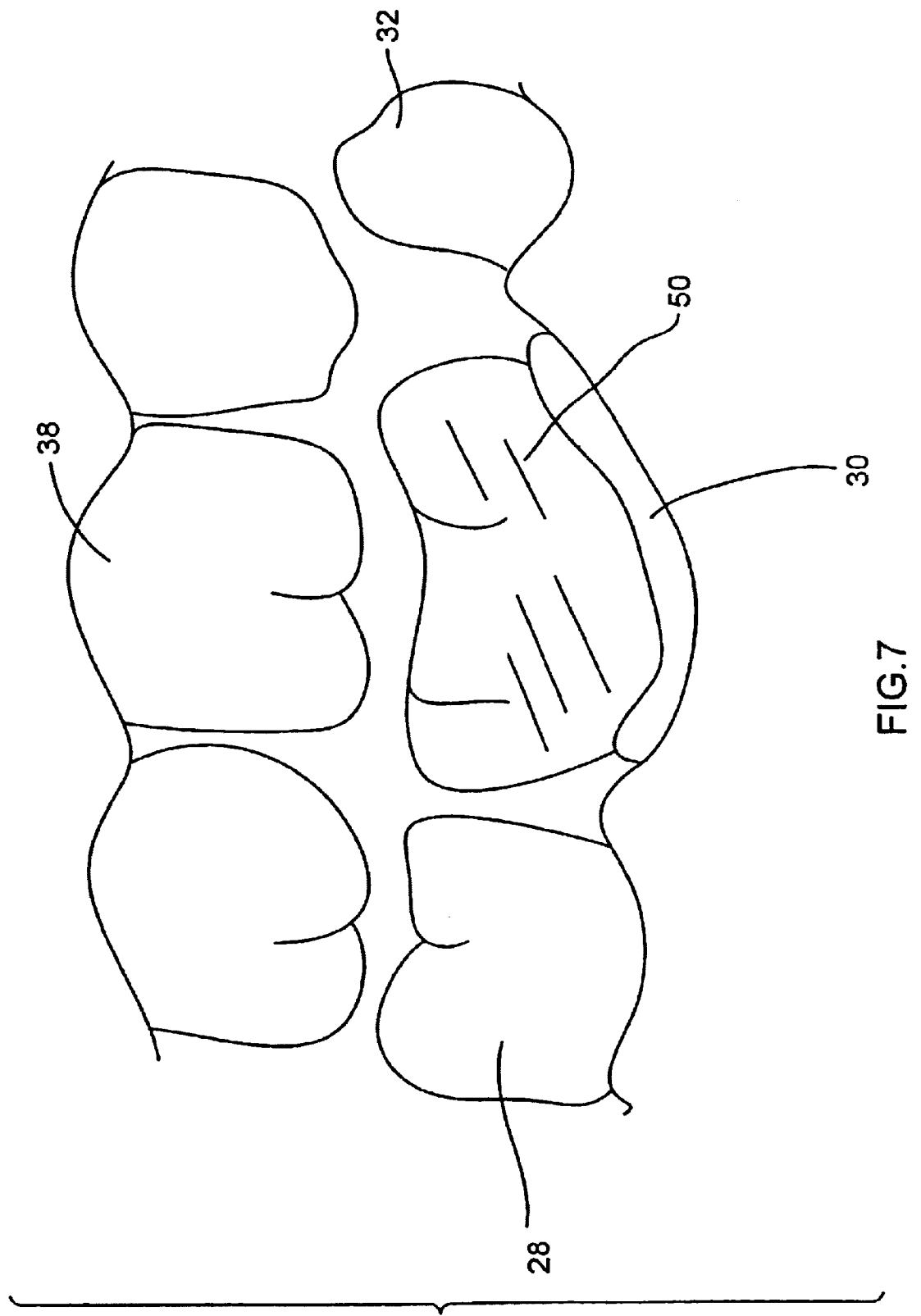
FIG. 7 illustrates the middle tooth of FIG. 3 after receiving a crown.

If loop 18 freely passes through gap 36, then sufficient material has been removed and no further tooth reduction is required. As such, a crown 50 may be placed upon tooth 30 as illustrated in FIG. 7 as is known in the art.

To avoid overly reducing tooth 30, the dentist may initially remove only a small portion of the tooth. Tool 10 may then be used to determine whether loop 18 will pass through gap 36. If not, additional material may be removed and the process repeated as many times as necessary in order to permit loop 18 to pass through gap 36. Further, in an alternative embodiment the dentist may initially use a tool that has a loop with a size that is smaller than the intended gap. Once this loop passes through the gap, the dentist knows that he or she is close to removing the appropriate amount of material. Additional material then may be removed and the measuring process repeated with a tool having a loop with the desired thickness of gap 36. Once this passes through the gap, an appropriate amount of material has been removed and the crown may be fabricated and applied.

As previously mentioned, the measuring tools may be constructed of disposable material so that they may simply be discarded after use. Conveniently, the measuring tools may be provided within sterile packaging so that they remain sterile until use. In some cases, it will be appreciated that sterilizable materials may be used to construct the measuring tools so that they may be reused after appropriate sterilization.

Figure 8:
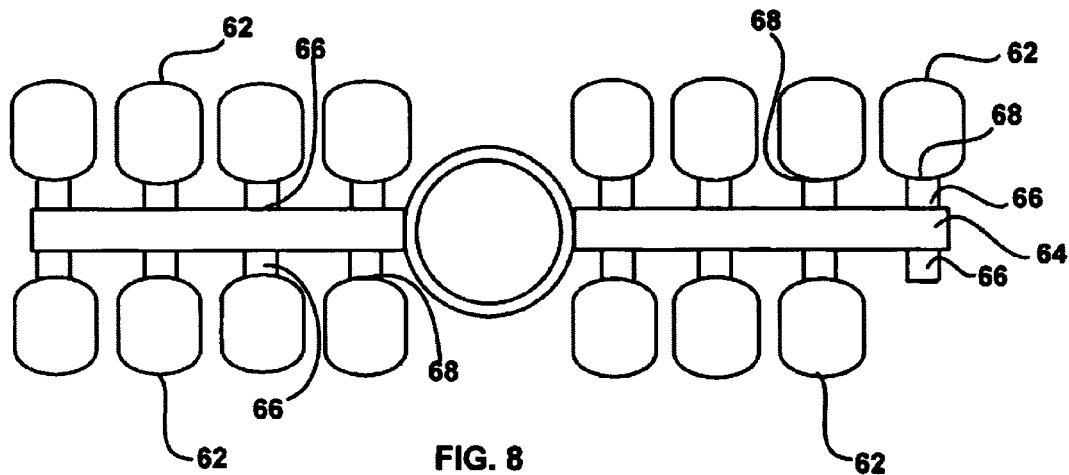
FIG. 8 illustrates a set of flexible loops that may be used to measure the amount of tooth reduction according to the invention.

Shown in FIG. 8 is a kit 60 containing a set of disposable flexible loops 62 that are held together by a frame 64. Flexible loops 62 may be constructed of any of the materials described herein. In one specific application, loops 62 may be constructed of an occlusal marking paper so that when loop 62 comes into contact with a tooth, a mark will appear at the point of contact. In such cases, frame 64 may include tabs 66 that are also constructed of an occlusal marking paper having score lines 68 adjacent to loops 62. In this way, loops 62 may easily be removed from frame 64 by tearing the paper along score lines 68.

Loops 62 may be used with essentially any type of tool capable of holding the loop and positioning it within a patient's mouth. Examples of suitable tools include those with jaws, clips, retractable hooks or the like that may grasp loop 62.

Figure 9:
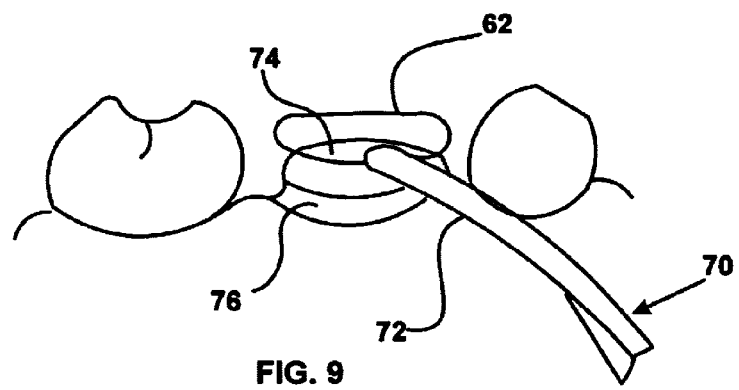
FIG. 9 illustrates an alternative method for measuring the amount of tooth reduction using a flexible loop that is removably held by a holding device according to the invention.
Figure 10:
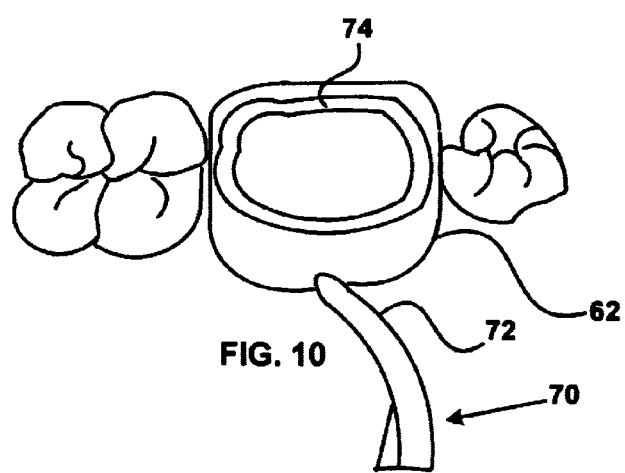
FIG. 10 illustrates the method of FIG. 9 from a top view.

One example of a procedure where one of the loops 62 is used to measure the amount of tooth reduction is illustrated in FIGS. 9 and 10. Loop 62 is held by a hemostat 70 having a pair of jaws 72. Hemostat 70 may be used to grasp loop 62 either before or after being removed from frame 64. Hemostat 70 includes a pair of handles as is known in the art to operate jaws 72. Another example of a suitable hemostat is described in, for example, U.S. Pat. No. 5,931,843, the complete disclosure of which is herein incorporated by reference.

Once held by hemostat 70, loop 62 may be used with any of the procedures and techniques described herein. For example, as shown in FIGS. 9 and 10, loop 62 may be positioned over a reduced portion 74 of a tooth 76 to measure the amount of tooth reduction in a manner to that previously described. Because loop 62 is constructed of a marking material, marks will be left on the areas of loop 62 that come into contact with a tooth when pulling loop 62 between the opposing teeth.

Following use, jaws 72 may be separated and loop 62 removed. Loop 62 may then be discarded. Following sterilization, hemostat 70 may be reused with another loop 62.

The invention has now been described in detail for purposes of clarity and understanding. However, it will be appreciated that certain changes and modifications may be practiced within the scope of the appending claims.

What is claimed is:

1. A tooth reduction measuring system, comprising:
    a holding tool having a proximal end and a distal end, wherein the distal end includes a connector; and
    a flexible loop that is configured to be coupled to the holding tool by the connector, wherein the loop has a thickness in the range from about 1 mm to about 2 mm, wherein the loop defines an opening that is sized large enough to be placed around a tooth, wherein and a cross sectional area of the opening is in the range from about 25 mm$^2$ to about 175 mm$^2$, and wherein the loop is adapted to be positioned relative to a pair of opposing teeth, one of which has been reduced, such that the pair of opposing teeth are within the opening, and wherein the loop is adapted to be pulled by the holding tool into a gap between the opposing teeth to permit evaluation of the size of the gap based on the thickness of the loop; and
    wherein the loop extends at an angle from the holding tool at an angle in the range from about 1 to about 90 degrees.

2. A system as in claim 1, wherein the loop is constructed of a polymer.

3. A system as in claim 1, wherein the loop is removably attached to the connector.

4. A system as in claim 3, wherein the loop extends from the tool at an acute angle.

5. A system as in claim 1, wherein the connector comprises a set of jaws into which the loop may be held, and wherein the tool includes a pair of handles to open and close the jaws.

6. A system as in claim 1, further comprising a marking material on the loop that produces a mark on the loop where the loop contacts the tooth.

7. A system as in claim 1, wherein the tool is selected from a group of tools consisting of hemostats, clamps and forceps.

8. A tooth reduction measuring system, comprising:
    a flexible loop having a thickness in the range from about 1 mm to about 2 mm, wherein the loop defines an opening that is sized large enough to be placed around a tooth, and wherein the loop is adapted to be positioned relative to a pair of opposing teeth, one of which has been reduced, such that the pair of opposing teeth are within the opening, and wherein the loop is adapted to be pulled by the holding tool into a gap between the opposing teeth to permit evaluation of the size of the gap based on the thickness of the loop, wherein and a cross sectional area of the opening is in the range from about 25 mm$^2$ to about 175 mm$^2$; and
    a marking material on the loop that produces a mark on the loop where the loop contacts the tooth.

9. A system as in claim 8, further comprising a frame to which the loop is removably coupled.

10. A method for evaluating the amount of tooth reduction, the method comprising:
    providing a holding tool having a proximal end and a distal end;
    coupling a flexible loop to the distal end, and wherein the loop has a thickness in the range from about 1 mm to about 2 mm;
    grasping the tool and placing the loop generally around or adjacent to a reduced tooth;
    instructing a patient to bite down to move an opposing tooth generally adjacent the reduced tooth;
    retracting the tool to pull the loop into a gap between the reduced tooth and the opposing tooth; and
    evaluating the size of the gap based on the thickness of the loop relative to the gap.

11. A method as in claim 10, wherein the loop includes a marking material that marks the loop where the loop contacts the reduced tooth or the opposing tooth, and further comprising evaluating the loop for any marks that are indicative of areas where the reduced tooth may be further reduced.

12. A method as in claim 10, further comprising removing the loop from the tool and sterilizing the tool.

13. A method as in claim 10, further comprising separating the loop from a frame prior to coupling the loop to the distal end.

14. A method for placing a crown onto a target tooth of a patient, the method comprising:
    removing tooth structure from the target tooth;
    providing a holding tool having a proximal end and a distal end;
    coupling a flexible loop to the distal end, wherein the loop has a thickness in the range from about 1 mm to about 2 mm;

grasping the tool and placing the loop generally around or adjacent to the target tooth;

instructing the patient to bite down to move an opposing tooth generally adjacent the target tooth;

retracting the tool to pull the loop into a gap between the target tooth and the opposing tooth;

evaluating the size of the gap based on the thickness of the loop relative to the gap;

removing additional tooth structure from the target tooth or the opposing tooth if the loop is unable to move through the gap; and placing a crown onto the target tooth.

15. A method as in claim 14, wherein the loop comprises a first loop having a first loop thickness, and further comprising removing the first loop from the tool and coupling a second loop having a second loop thickness, and pulling the second loop into the gap if the first loop is able to pass through the gap.

16. A method as in claim 14, wherein the loop includes a marking material that marks the loop where the loop contacts the reduced tooth or the opposing tooth, and further comprising evaluating the loop for any marks and removing additional material from the target tooth in areas that correspond to the marked areas on the loop.

17. A method as in claim 14, further comprising removing the loop from the tool, and disposing the loop after its use.

18. A method as in claim 14, wherein the loop extends from the tool at an acute angle, wherein the loop is placed about a rear tooth.

19. A method as in claim 14, further comprising making an impression of the target tooth, and fabricating the crown based on the impression.

20. A method as in claim 14, further comprising bonding the crown to the target tooth.

* * * * *